United States Patent [19]

Averill et al.

[11] Patent Number: 4,921,500
[45] Date of Patent: May 1, 1990

[54] FEMORAL HEAD ADAPTOR FOR INTEROPERATIVE ASSEMBLY

[75] Inventors: Robert G. Averill, Ringwood; Paul Serekian, Glen Rock; Scott K. Taylor, Ridgewood, all of N.J.

[73] Assignee: Osteonics Corp., Allendale, N.J.

[21] Appl. No.: 316,855

[22] Filed: Feb. 28, 1989

[51] Int. Cl.$^5$ .............................................. A61F 5/04
[52] U.S. Cl. ........................................ 623/22; 623/18
[58] Field of Search .............. 128/92 YV; 623/18, 22, 623/23

[56] References Cited

U.S. PATENT DOCUMENTS

| 4,032,994 | 7/1977 | Frey | 623/22 |
| 4,058,856 | 11/1977 | Doerre et al. | 623/22 |
| 4,750,905 | 6/1988 | Koeneman et al. | 623/22 |

FOREIGN PATENT DOCUMENTS

| 0193681 | 9/1986 | European Pat. Off. | 623/18 |
| 2724041 | 11/1978 | Fed. Rep. of Germany | 623/18 |
| 2598609 | 11/1987 | France | 623/22 |

Primary Examiner—Robert A. Hafer
Assistant Examiner—Beth Anne Cicconi
Attorney, Agent, or Firm—Samuelson & Jacob

[57] ABSTRACT

An adaptor is interposed between a socket in a ceramic femoral head component and a post on a femoral stem component in the femoral stem of a prosthetic hip joint to enable the use of a taper within the socket which is steeper than the taper on the post so as to reduce hoop stresses in the ceramic femoral head component while at the same time accomplishing securement of the ceramic femoral head component upon the post of the existing femoral stem component.

14 Claims, 1 Drawing Sheet

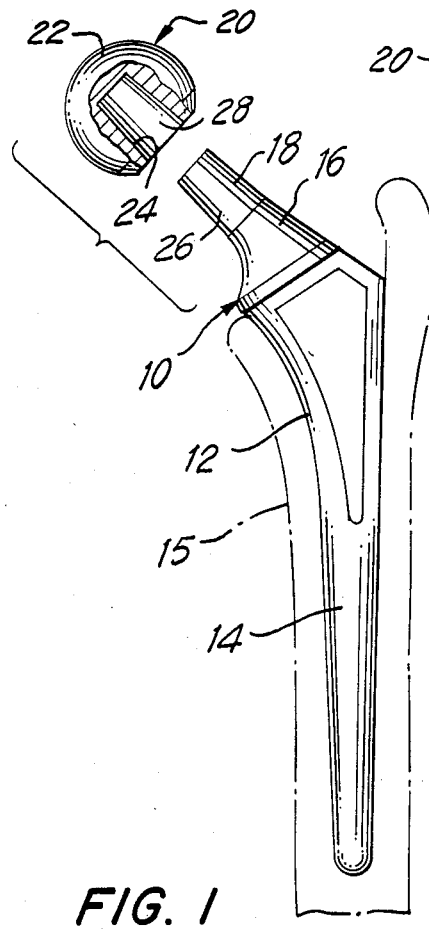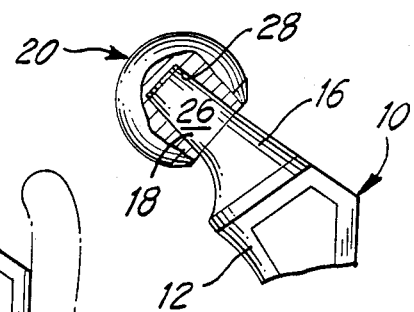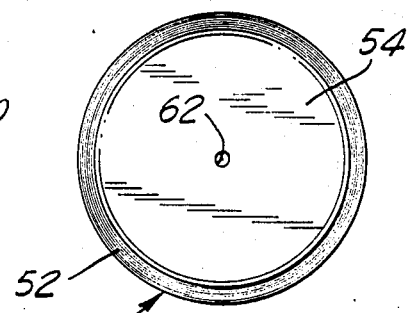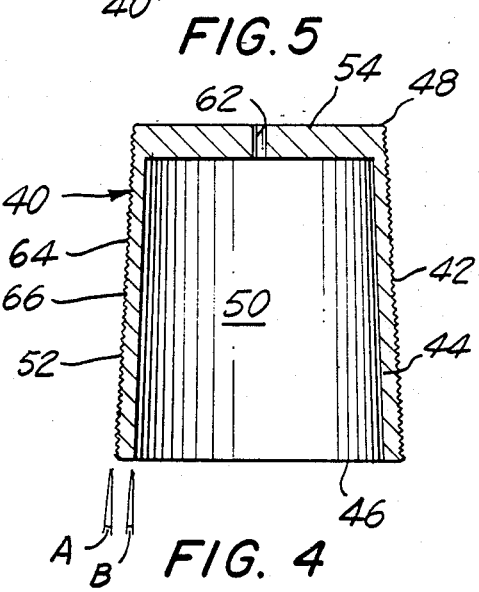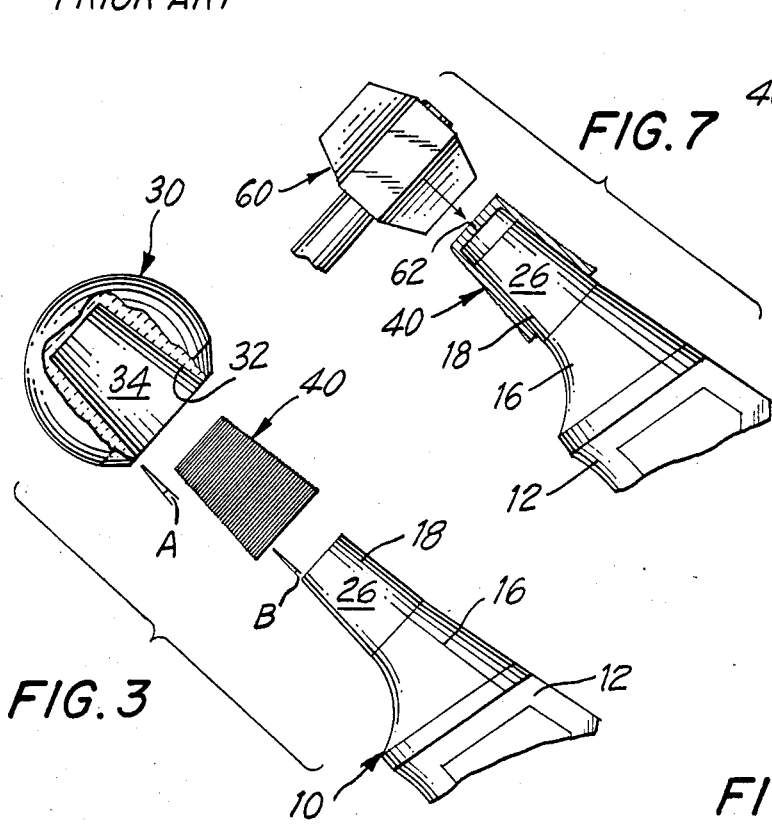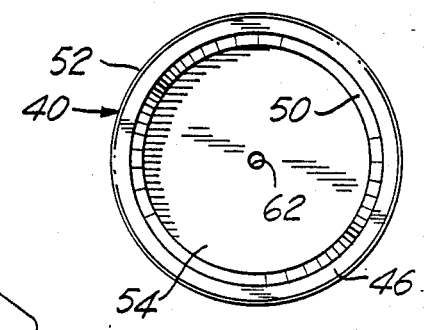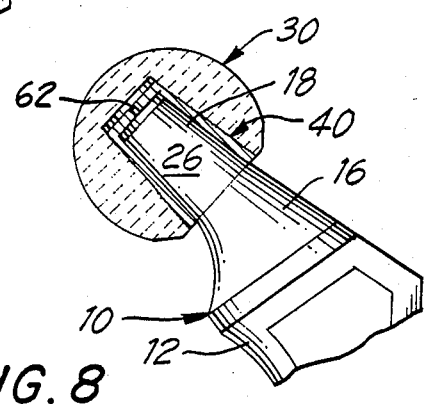
U.S. Patent — May 1, 1990 — 4,921,500
FIG. 1 PRIOR ART
FIG. 2 PRIOR ART
FIG. 3
FIG. 4
FIG. 5
FIG. 6
FIG. 7
FIG. 8

FEMORAL HEAD ADAPTOR FOR INTEROPERATIVE ASSEMBLY

The present invention relates generally to prosthetic implants and pertains, more specifically, to femoral implants of the type in which a femoral head is assembled with a femoral stem in a prosthetic hip joint.

The use of prosthetic implant devices in the human body for replacing defective, damaged or diseased anatomical joints of the body has become quite well known. One of the more common forms of implant devices is the hip joint prosthesis which provides an interconnection between the femur and the acetabular socket of the pelvis. Conventional prosthetic hip joints usually include a femoral component having a spherical head member affixed to the femur by means of a femoral stem secured within the femur. Often, the spherical head member is in the form of a separate component part assembled and is assembled with a femoral stem component by means of an interference fit between a tapered post on the femoral stem component and a complementary socket in the spherical head component. Usually, the spherical head component and the femoral stem component are constructed of a biocompatible metal, such as a cobalt-chrome alloy, and the taper provided on the post and in the socket conforms to a known standard taper configuration for the joining of such metallic component parts.

More recently, it has been suggested that spherical head components constructed of ceramic materials possess certain properties which render these particular components preferable over metallic spherical head components, under certain circumstances. In those instances where a surgeon determines that a ceramic head component is preferable, it would be advantageous to be able merely to employ a ceramic head component, rather than a metallic head component, in connection with an available femoral stem component. However, the tapers provided for the assembly of a metallic head component with the femoral stem component are not compatible with a ceramic head component in that the ceramic materials cannot tolerate the high levels of hoop stress developed upon assembly of the respective tapered socket and post and consequently must be provided with a socket having a much steeper taper than is found on the post of the available femoral stem component. While it may be feasible to construct a femoral stem component with a post of suitable taper to match the taper required in a ceramic head component, it would be more advantageous to be able to employ existing femoral stem components with ceramic head components, thereby enabling use of the existing femoral stem components with either a metallic head component or a ceramic head component.

The present invention provides an adaptor for use in connection with existing femoral stem components to enable selective securement of a ceramic femoral head component on the post of an existing femoral stem component, and has several objects and advantages, some of which are summarized as follows: Allows the use of existing conventional femoral stem components in connection with ceramic head components in a prosthetic hip joint; enables the securement of a ceramic head component upon the post of an existing conventional femoral stem component interoperatively at an implant site; provides a secure connection between a ceramic head component and a femoral stem component, utilizing an interference fit between complementary tapered surfaces of the components, without developing excessive stress in the ceramic head component; enables the selection of either a metallic head component or a ceramic head component for use in connection with a particular femoral stem component, and eases the assembly of the selected head component with the stem component; allows the use of a ceramic head component at implant sites already provided with an implanted conventional femoral stem of the type heretofore not compatible with a ceramic head component; and facilitates generally the implant of a femoral prosthesis having a ceramic head component.

The above objects and advantages, as well as further objects and advantages, are attained by the present invention, which may be described briefly as an adaptor for use in assembling and securing together a ceramic femoral head component of a prosthetic hip joint and a femoral stem component of the prosthetic hip joint, the femoral stem component including a post having an outer seating surface tapered at a first taper, and the ceramic femoral head including a socket having an inner seating surface tapered at a second taper steeper than the first taper, the adaptor comprising: a cup-like body member constructed of a biocompatible metal and having a frusto-conical wall extending axially between a first end and a second end, the diameter of the body member being larger at the first end than the diameter of the body member at the second end; the body member being open at the first end thereof and including a frusto-conical inner surface extending inside the body member, along the wall thereof, from the open first end toward the second end, the inner surface having a taper complementary to the first taper and the relative dimensions of the inner surface of the body member and the outer seating surface of the post being such that the post is receivable within the body member for seating of the body member upon the post in secured relationship therewith; a frusto-conical outer surface on the body member, the outer surface extending outside the body member, along the wall thereof, between the first end and the second end and having a taper complementary to the second taper such that the thickness of the wall varies axially along the wall from a greater thickness adjacent the first end to a lesser thickness adjacent the second end, the relative dimensions of the outer surface of the body member and the inner seating surface of the socket being such that the body member is receivable within the socket for seating of the ceramic femoral head component upon the body member in secured relationship therewith; and a web extending transversely across the body member at the second end thereof for reinforcing the wall of the body member adjacent the second end against forces exerted on the body member, adjacent the second end thereof, during assembly. The invention will be understood more fully, while still further objects and advantages will become apparent, in the following detailed description of a preferred embodiment of the invention illustrated in the accompanying drawing, in which:

FIG. 1 is an exploded elevational view, partially sectioned, illustrating a conventional femoral stem component and femoral head component, about to be assembled;

FIG. 2 is a fragmentary longitudinal cross-sectional view of the components of FIG. 1 assembled;

FIG. 3 is a fragmentary exploded elevational view, partially sectioned, similar to FIG. 1, but illustrating the use of an adaptor constructed in accordance with the present invention in connection with the securement of a ceramic femoral head component upon the femoral stem component;

FIG. 4 is an elevational cross-sectional view of the adaptor;

FIG. 5 is a top plan view of the adaptor;

FIG. 6 is a bottom plan view of the adaptor;

FIG. 7 is a fragmentary longitudinal cross-sectional view showing installation of the adaptor on the femoral stem component; and FIG. 8 is a fragmentary longitudinal cross-sectional view showing the ceramic femoral head component assembled with and secured to the femoral stem component, utilizing the adaptor.

Referring now to the drawing, and especially to FIGS. 1 and 2 thereof, a conventional femoral stem 10 is seen to have a stem component 12 including a stem 14 extending longitudinally in a downward, or inferior direction for reception within a femur, shown in phantom at 15, in a now well-known manner, to provide for replacement of the natural femoral head with a prosthetic femoral head. The femoral stem component 12 includes a neck 16 extending upwardly, in a superior direction, and carrying a post 18 unitary with the neck 16. A femoral head component 20 has a spherical outer surface 22 and is assembled with the stem component 12 by means of a socket 24 which is fitted onto the post 18. The outer seating surface 26 of the post 18 is tapered, and the inner seating surface 28 of the socket 24 is provided with a complementary taper so that upon appropriate seating of the femoral head component 20 upon the femoral stem component 12, the seating surfaces 26 and 28 will engage one another. The relative dimensions of the seating surfaces 26 and 28 are such that upon such engagement, an interference fit will secure the head component 20 to the stem component 12. In this manner, the femoral stem 10 is a part of a modular system enabling a surgeon to choose any one of several femoral head components for assembly with any one of several femoral stem components to construct a femoral stem best suited for a particular implant site.

Both the femoral stem component 12 and the femoral head component 20 are constructed of a biocompatible metal, such as a cobalt-chrome alloy, and the taper provided along the post 18 and the socket 24 is a conventional taper connection, such as a Brown and Sharpe taper, which accomplishes the desired securement upon assembly. The use of the taper connection also allows selective removal of the femoral head component 20 from the femoral stem component 12, should such removal become necessary. Under certain circumstances, some surgeons prefer to employ a ceramic femoral head component instead of a metallic femoral head component so as to take advantage of the properties offered by a ceramic femoral head for a particular implant site. For this reason, it would be advantageous if the metallic and ceramic femoral head components could be fully interchangeable so that either of the femoral head components could be utilized selectively with a particular single femoral stem component, thereby preserving the modularity of the system while minimizing the number and complexity of the components of the system. Moreover, such complete interchangeability would enable the choice of either a metallic or a ceramic femoral head component for interoperative assembly with the femoral stem component, after the femoral stem component is implanted. However, ceramic materials suitable for use in a femoral head component are frangible when compared to metals and it has been found that the standard taper connections, such as the Brown and Sharpe taper, employed for the securement of a metallic femoral head component to the femoral stem component establishes hoop stresses within the ceramic femoral head, which hoop stresses exceed the strength of the material in tension, with catastrophic results. It has been found that these hoop stresses can be reduced to a tolerable level and that the ceramic femoral head can be secured to the stem component by means of a taper connection if the ceramic femoral head component is provided with a socket having a taper steep enough to accomplish a sufficient reduction in hoop stress, while still enabling securement by means of an interference fit. However, the requisite taper is steeper than that found in existing conventional femoral head components, and the corresponding femoral stem components, so that a ceramic femoral head component will not be directly interchangeable with a corresponding metallic femoral head component for securement to a given femoral stem component.

The present invention provides an adaptor which is used in connection with the assembly of a ceramic femoral head component with a femoral stem component to enable such assembly with and securement of the ceramic femoral head component to an existing femoral stem component. Thus, as seen in FIG. 3, a ceramic femoral head component 30 has a socket 32 with an inner seating surface 34. Inner seating surface 34 has a frusto-conical configuration and is tapered at a taper which is steeper than the taper provided along the outer seating surface 26 of post 18 of the existing femoral stem component 12. That is, the angle A of the taper of the inner seating surface 34 is greater than the angle B of the taper of the outer seating surface 26. Preferably, angle A is about twice angle B, angle A being approximately 6° while angle B is about 3°. In order to enable securement of the ceramic femoral head component 30 upon the femoral stem component 12, an adaptor 40 is interposed between the inner and outer seating surfaces 34 and 26.

As best seen in FIGS. 4 through 6, adaptor 40 has a cup-like body member 42 with a frusto-conical wall 44 extending between a lower, or inferior, end 46 and an upper, or superior, end 48. The diameter of the body member 42 at the lower end 46 is greater than the diameter at the upper end 48. The body member 42 is open at the lower end 46 and a frusto-conical inner surface 50 extends along the inside of the body member 42, along the wall 44, from the open lower end 46 to the upper end 48. A frusto-conical outer surface 52 extends along the wall 44 on the outside of the body member 42 between the lower end 46 and the upper end 48. A web 54 extends transversely across the body member 42 at the upper end 48 and serves to reinforce the wall 44, as will be explained in greater detail below.

The inner surface 50 has a taper complementary to the taper on the outer seating surface 26 of the post 18, and the relative dimensions of the inner surface 50 and the outer seating surface 26 are such that the adaptor 40 may be fitted over the post 18 and affixed thereto by an interference fit. Thus, as illustrated in FIG. 7, adaptor 40 is placed over post 18 and is urged into seated engagement with the post 18 by applying a downward force to the upper end 48, as by tapping the upper end 48 with a mallet 60 until the adaptor 40 is seated upon the post 18, as illustrated in FIG. 8. The web 54 reinforces the upper end 48 of the wall 44 against the forces applied by the mallet 60 so as to maintain the integrity of the adaptor 40. To this end, the wall thickness of the web 54 is greater than the wall thickness of the frusto-conical wall 44. A vent passage 62, located in the center of the web 54, passes through the web 54 and opens communication between the inside and the outside of the adaptor 40 during installation so that air and other matter which might otherwise be trapped between the adaptor 40 and the post 18 is expelled and will not interfere with the complete seating of the adaptor 40 on the post 18.

The outer surface 52 of the body member 42 has a taper complementary to the taper of the inner seating surface 34 of the socket 32 in the ceramic femoral head component 30 so that once the adaptor 40 is seated upon the post 18, as seen in FIG. 8, the ceramic femoral head component 30 is placed over the adaptor 40 and is urged into seated relationship therewith. The relative dimensions of the outer surface 52 and the inner seating surface 34 are such that upon such seating of the ceramic femoral head component 30 upon the adaptor 40, the ceramic femoral head component 30 is secured with an interference fit. In order to assist in that securement, the outer surface 52 preferably is provided with supplemental gripping means in the form of alternating ridges 64 and grooves 66 extending circumferentially around the outer surface 52. The steeper taper along the outer surface 52, and the corresponding steeper taper along the inner seating surface 34, assure that the assembly is completed and securement of the ceramic femoral head component 30 is effected without excessive hoop stresses which could damage the material of the ceramic femoral head component 30. At the same time, the existing femoral stem component 12 is rendered usable with the ceramic femoral head component 30, as well as with the metallic femoral head component 20.

Assembly of either of the femoral head components 20 or 30 is accomplished readily interoperatively, at the selection of the surgeon. Once the assembly is complete, the adaptor 40 is fully interposed between the ceramic femoral head component 30 and the post 18, since the difference between the taper of the outer surface 52 of the wall 44 and the taper of the inner surface 50 establishes a thickness in the wall 44 which varies from a greater thickness at the open lower end 46 of the wall 44 to a lesser thickness at the reinforced upper end 48 of the wall 44, with the result that the assembly is provided with a high degree of structural integrity. The adaptor 40 is constructed of a biocompatible metal, such as a titanium alloy.

It will be seen that the adaptor of the present invention allows the use of existing conventional femoral stem components in connection with ceramic femoral head components in a prosthetic hip joint; enables the securement of a ceramic femoral head component upon the post of an existing conventional femoral stem component interoperatively at an implant site; provides a secure connection between a ceramic femoral head component and a femoral stem component utilizing an interference fit between complementary tapered surfaces of the components, without developing excessive stress in the ceramic femoral head component; enables the selection of either a metallic femoral head component or a ceramic femoral head component for use in connection with a particular femoral stem component and eases the assembly of the selected head component with the stem component; allows the use of a ceramic femoral head component at implant sites already provided with an implanted conventional femoral stem of the type heretofore not compatible with a ceramic femoral head component; and facilitates generally the implant of a femoral prosthesis having a ceramic femoral head component.

It is to be understood that the above detailed description of a preferred embodiment of the invention is provided by way of example only. Various details of design and construction may be modified without departing from the true spirit and scope of the invention as set forth in the appended claims.

The embodiments of the invention in which an exclusive property or privilege is claimed are defined as follows:

1. An adaptor for use in assembling and securing together a ceramic femoral head component of a prosthetic hip joint and a femoral stem component of the prosthetic hip joint, the femoral stem component including a post having an outer seating surface tapered at a first taper, and the ceramic femoral head including a socket having an inner seating surface tapered at a second taper steeper than the first taper, the adaptor comprising:

a cup-like body member constructed of a biocompatible metal and having a frusto-conical wall extending axially between a first end and a second end, the diameter of the body member being larger at the first end than the diameter of the body member at the second end;

the body member being open at the first end thereof and including a frusto-conical inner surface extending inside the body member, along the wall thereof, from the open first end toward the second end, the inner surface having a taper complementary to the first taper and the relative dimensions of the inner surface of the body member and the outer seating surface of the post being such that the post is receivable within the body member for seating of the body member upon the post in secured relationship therewith;

a frusto-conical outer surface on the body member, the outer surface extending outside the body member, along the wall thereof, between the first end and the second end and having a taper complementary to the second taper such that the thickness of the wall varies axially along the wall from a greater thickness adjacent the first end to a lesser thickness adjacent the second end, the relative dimensions of the outer surface of the body member and the inner seating surface of the socket being such that the body member is receivable within the socket for seating of the ceramic femoral head component upon the body member in secured relationship therewith; and a web extending transversely across the body member at the second end thereof for reinforcing the wall of the body member adjacent the second end against forces exerted on the body member, adjacent the second end thereof, during assembly.

2. The invention of claim 1 including a vent opening in the web, the vent opening extending between the inside and the outside of the body member.

3. The invention of claim 2 wherein the vent opening is centered within the web.

4. The invention of claim 1 including gripping means along the outer surface of the body member for gripping the socket of the ceramic femoral head when the inner seating surface is seated upon the outer surface.

5. The invention of claim 4 wherein the gripping means includes circumferential grooves and ridges on the outer surface.

6. The invention of claim 5 including a vent opening in the web, the vent opening extending between the inside and the outside of the body member.

7. The invention of claim 6 wherein the vent opening is centered within the web.

8. The invention of claim 1 wherein the taper of the outer surface is about twice as steep as the taper of the inner surface.

9. The invention of claim 8 wherein the taper of the outer surface is about 6° and the taper of the inner surface is about 3°, relative to the axial direction.

10. The invention of claim 8 including a vent opening in the web, the vent opening extending between the inside and the outside of the body member.

11. The invention of claim 8 including gripping means along the outer surface of the body member for gripping the socket of the ceramic femoral head when the inner seating surface is seated upon the outer surface.

12. The invention of claim 11 wherein the gripping means includes circumferential grooves and ridges on the outer surface.

13. The invention of claim 8 wherein the web has a wall thickness greater than the thickness of the frusto-conical wall.

14. The invention of claim 1 wherein the web has a wall thickness greater than the thickness of the frusto-conical wall.

* * * * *